(12) United States Patent
Jiang et al.

(10) Patent No.: US 9,105,456 B2
(45) Date of Patent: Aug. 11, 2015

(54) TANDEM MASS SPECTRUM ANALYSIS DEVICE AND MASS SPECTRUM ANALYSIS METHOD

(75) Inventors: Gongyu Jiang, Shanghai (CN); Hui Mu, Shanghai (CN); Li Ding, Manchester (GB)

(73) Assignee: SHIMADZU RESEARCH LABORATORY (SHANGHAI) CO. LTD., Shanghai (CN)

( * ) Notice: Subject to any disclaimer, the term of this patent is extended or adjusted under 35 U.S.C. 154(b) by 57 days.

(21) Appl. No.: 13/576,294

(22) PCT Filed: Jan. 26, 2011

(86) PCT No.: PCT/CN2011/070657
§ 371 (c)(1),
(2), (4) Date: Jul. 31, 2012

(87) PCT Pub. No.: WO2011/095098
PCT Pub. Date: Aug. 11, 2011

(65) Prior Publication Data
US 2012/0292498 A1  Nov. 22, 2012

(30) Foreign Application Priority Data
Feb. 5, 2010 (CN) .......................... 2010 1 0301257

(51) Int. Cl.
*H01J 49/06* (2006.01)
*H01J 49/00* (2006.01)
(Continued)

(52) U.S. Cl.
CPC ............. *H01J 49/063* (2013.01); *H01J 49/004* (2013.01); *H01J 49/062* (2013.01); *H01J 49/4215* (2013.01); *H01J 49/4225* (2013.01); *G01N 30/7206* (2013.01)

(58) Field of Classification Search
CPC ...... H01J 49/421; H01J 49/062; H01J 49/063
USPC ................................................. 250/281, 282
See application file for complete search history.

(56) References Cited

U.S. PATENT DOCUMENTS 5,420,425 A   5/1995   Bier et al.
6,949,743 B1  9/2005   Schwartz
(Continued)

FOREIGN PATENT DOCUMENTS

CN   101126737 A  *  2/2008
CN   101373695 A     2/2009

OTHER PUBLICATIONS

Makarov, Alexander, "Orbitrap Mass Spectrometry: from Dream to Mainstream", Sep. 9, 2009, Lunch talk at 18th IMSC Bremen. Fetched from archive.org (Feb. 14, 2010). http://web.archive.org/web/20100214060036/http://thermo.com/eThermo/CMA/PDFs/Various/File_52781.pdf.*

*Primary Examiner* — Jack Berman
*Assistant Examiner* — James Choi
(74) *Attorney, Agent, or Firm* — Tim Tingkang Xia, Esq.; Locke Lord LLP (57) ABSTRACT

A tandem mass spectrometer is provided in the present invention. The mass spectrometer includes an ion source, a quadrupole mass filter located at downstream side of the ion source, a linear ion trap disposed at downstream side of the mass filter and an ion detector placed on the side of the ion trap, all of which are placed in a vacuum environment. The instrument can obtain MS meeting the standard spectral library search criteria by the quadrupole mass filter cooperating with linear ion trap, realize any multi-stage MS under two modes of axial collision and resonance excitation, and predict and optimize the inflow amount and types of samples under the ion trap analysis mode by the quadrupole. A tandem MS analysis method is also provided, which can repeatedly provide precursor ion selection, ion acceleration, achieve high-energy collision dissociation, low product ion mass discrimination effect.

23 Claims, 5 Drawing Sheets (51) Int. Cl.
*H01J 49/42* (2006.01)
*G01N 30/72* (2006.01)

(56) References Cited

U.S. PATENT DOCUMENTS

| | | | |
|---|---|---|---|
| 7,582,866 B2 | 9/2009 | Furuhashi et al. | |
| 8,624,181 B1 * | 1/2014 | Newton | 250/287 |
| 2004/0164240 A1 | 8/2004 | Okumura et al. | |
| 2004/0222370 A1 * | 11/2004 | Bateman et al. | 250/281 |
| 2005/0023461 A1 * | 2/2005 | Schubert et al. | 250/306 |
| 2007/0029473 A1 * | 2/2007 | Verentchikov | 250/281 |
| 2008/0035842 A1 * | 2/2008 | Sudakov et al. | 250/287 |
| 2008/0073515 A1 * | 3/2008 | Schoen | 250/292 |
| 2008/0191129 A1 * | 8/2008 | Makarov et al. | 250/282 |
| 2009/0302215 A1 * | 12/2009 | Guna et al. | 250/283 |
| 2010/0237236 A1 * | 9/2010 | Thomson et al. | 250/283 |
| 2010/0237237 A1 * | 9/2010 | Green et al. | 250/283 |
| 2011/0084205 A1 * | 4/2011 | Makarov et al. | 250/282 |

\* cited by examiner

TANDEM MASS SPECTRUM ANALYSIS DEVICE AND MASS SPECTRUM ANALYSIS METHOD

BACKGROUND OF THE INVENTION

1. Field of Invention

The present invention relates to a tandem mass spectrum analysis device and a tandem mass spectrum analysis method, and more particularly, to a multi-mode analysis device and method for realizing single-stage to multi-stage mass spectrometry with a quadrupole mass filter combined with an ion trap.

2. Related Art

Chromatography-mass spectrometer, especially gas chromatography-mass spectrometer is playing an increasingly important role with rising demand in analysis field as industrial production, environmental monitoring. New technologies are emerging in all the sub-field of chromatography, mass spectrometry, and their interfaces, and help to increase the kinds of instrument. In terms of the mass spectrometry, the mass spectrometer for gas chromatography connection has been developed from the initial magnetic fan mass spectrometer to the single quadrupole mass spectrometer, ion trap mass spectrometer, and time-of-flight mass spectrometer that are widely used at present. The price of the instrument decreases significantly, and the analysis efficiency is increased. To effectively resolve some complex unknown samples, a tandem mass spectrometer is developed to make tandem mass spectrometry (MSn) for separated products of the gas chromatography. The tandem mass spectrometer combined with the gas chromatography is mainly classified in an ion trap mass spectrometer and a triple quadrupole mass spectrometer. The triple quadrupole mass spectrometer adds an ion collision chamber and a second quadrupole analyzer after a first quadrupole analyzer. The first quadrupole analyzer selects one of ions (possibly caused by poor separation of previous chromatography) or multiple fragment ions generated by the ion source and enables the selected ion to enter the collision chamber through the analyzer to perform collision dissociation with neutral gas atoms, and fragment product ions thereof enter the second quadrupole analyzer for analysis, so as to obtain a second-stage mass spectrum. When the chromatography has complex composition co-eluting, the second-stage mass spectrum has higher signal-to-background ratio and quantitative accuracy than the single-stage mass spectrum, and structure information of the analyzed ions can also be obtained.

When people want to further resolve the structure of the collision product ions, the demand of MS" for mass spectra of more than three stages is put forward, the triple quadrupole analyzer is unable to do that, but the ion trap good at MS" (n>=3) exhibits its superiority.

Early in the 1980s, the Finnigan Company in U.S. produced a chromatography-mass spectrometer like a gas chromatography three-dimensional (3D) ion trap detector, which can make tandem mass spectrometry for multiple times, has a low price, and is widely used until today. However, a 3D quadrupole ion trap has the following problems in the combination with the gas chromatography:

1. Before precursor ion selection and mass scanning, the 3D quadrupole ion trap needs to cool and gather all the ions in a small area of the ion trap center, due to charge interactions among the ions, if the ion density is high, the ion resonance ejection process may be affected by the ion space charge, the resolution becomes poor, and the peak shifts. In other words, the space charge effect greatly limits the number of ions allowed by each operation. Since the number of the ions analyzed each time is limited (generally several hundreds to tens of thousands, depending on the mass-to-charge ratio range and the scan speed), this influences the dynamic range of the instrument analysis.

2. The gas chromatography-mass spectrometer widely uses an electron bombardment ion source (EI). Such an ion source generates a series of fragment ions in the ionization of sample molecules. Determining composition of a compound according to the fragment ion abundance proportional relation has become a standard analysis method. A standard database of thousands of samples has been formed for the most widely used (EI) quadrupole mass spectrometer, but because a longer ion storage time is required for analysis of the quadrupole ion trap, facilitating generation and transformation of fragment ions, resulting in a great difference between the fragment abundance relation in the quadrupole ion trap mass spectra and the fragment abundance relation in the quadrupole mass spectra, and a number of compounds cannot be accurately identified according to the standard database after being analyzed with an ion trap analyzer.

3. When an ion trap is used for tandem mass spectrometry, precursor ions must be excited first to obtain sufficient ionization kinetic energy, and then product ions can be got in collision with the gas molecules. To capture a precursor ion having sufficient kinetic energy in the ion trap, the stability parameter q of the precursor ion must be large enough, so as to obtain a sufficiently deep pseudopotential well. This will result in the lower mass limit of a fragment product ion, that is to say, if the mass of the fragment product ion is less than the lower mass limit corresponding to the q, the product ion cannot be captured by the ion trap, thereby causing ion loss. Generally, the lower mass limit of a product ion is one third of the mass of the precursor ion, which may limit the available mass range of multi-stage mass spectra.

With the invention of a linear ion trap, problems about ion volume and dynamic range of the 3D ion trap have been solved in a large extent. This has been described in U.S. Pat. No. 5,420,425 and No. US19960656954. However, when the linear ion trap is combined with an electron impact ionization source (EI), the cracking form varies greatly as compared with the quadrupole mass filter, which also causes serious problems for database retrieval. A digital wave-driven ion trap (Chinese Patent No. ZL200710045190) can rapidly change the value of q in the collision-induced dissociation (CID) process, which improves the contradictory problem between the product ion lower mass limit and the precursor ion excitation energy to some extent; this has been disclosed in U.S. Pat. No. 7,582,866 and U.S. Pat. No. 6,949,743. However, the methods disclosed cannot really realize the condition of high-energy CID used in the triple quadrupole instrument. Owing to the foregoing ion trap problems, although the linear ion trap has been successfully applied to the liquid chromatography mass spectrometry (LCMS), the linear ion trap has not yet been commercialized in the field of gas chromatography mass spectrometry (GCMS).

Objectives of the present invention are, first, finding a scheme of an instrument that is capable of realizing multi-stage tandem mass spectrometry (three stages or more), has high sensitivity and product ion output efficiency, and maintains higher dynamic ranges of first-stage mass spectra and second-stage mass spectra; and second, integrating two superiorities of the instrument, that is, the advantage of being easy to use database to make mass spectrum retrieval for the EI source fragment ions and the advantage of performing multi-stage tandem mass analysis to determine unknown compounds.

SUMMARY OF THE INVENTION

A mass spectrometer for analyzing gaseous components according to the present invention includes: an ion source in a vacuum environment; a quadrupole mass filter located downstream of the ion source; a linear quadrupole ion trap located downstream of the mass filter; and an ion detector disposed at a side of the linear ion trap, configured to receive ions extracted from the side outlet of the linear ion trap.

In the mass spectrometer according to the present invention, the quadrupole mass filter may include a rear short rod system, so as to enable ions selected by the quadrupole mass filter to efficiently enter the linear ion trap. A pulse gas providing device may be further included, so as to provide required cooling gas and collision gas for the linear ion trap.

In the mass spectrometer according to the present invention, a switching device is used to switch the voltage supplied to the electrodes of the linear ion trap from a high frequency trapping voltage to the a deflection voltage, so that ions passing through the quadrupole mass filter, after entering the linear ion trap, deflect towards the direction of the side outlet by the deflection formed by the deflection voltage, thereby being expelled to the ion detector from the outlet radially. In the mass spectrum obtained thereby, the abundance ratio of the fragment ion generated in the electron bombardment ionization source (EI source) may be consistent with that of the mass spectrum obtained by a single quadrupole mass filter spectrometer.

In the mass spectrometer according to the present invention, a high frequency trapping voltage may be applied to electrodes of the linear ion trap, so as to trap ions transmitted from the quadrupole mass filter, and the ions in the ion trap are selectively expelled to the detector in an order of mass-to-charge ratios through auxiliary resonance excitation, so as to form a mass spectrum.

In the mass spectrometer according to the present invention, a high frequency trapping voltage may be applied to electrodes of the linear ion trap, and an axial potential difference is generated between the quadrupole mass filter and the linear ion trap, in which the potential difference accelerates ions transmitted from the quadrupole mass filter and enables the ions to collide with the collision gas in the ion trap. By setting amplitude and frequency of the high frequency trapping voltage, product ions generated by collision dissociation can be captured by the ion trap. After being captured by the ion trap, the product ions are expelled to the detector in an order of mass-to-charge ratios through auxiliary resonance excitation, so as to form a second-stage mass spectrum. Meanwhile, it is also feasible, according to a selective resonance excitation method or an ion selection method using a and q stability diagrams, to remove unwanted ions according to a mass-to-charge ratio, retain product ions of a certain mass-to-charge ratio for continuous cracking, and expel fragmented ions to the detector in an order of mass-to-charge ratios through auxiliary resonance excitation, so as to form a third-stage mass spectrum.

The present invention provides a new method for performing mass filtering and dissociation on ions trapped in a linear ion trap using a quadrupole mass filter combined with the ion trap. The method includes setting high frequency and DC voltages on the quadrupole mass filter, so as to establish a quadrupole electric field allowing ions of a certain mass-to-charge ratio to pass; establishing a pulse extraction voltage pointing to the direction of the quadrupole mass filter in an axial direction of the linear ion trap, ejecting ions in the linear ion trap to enter the quadrupole mass filter, and establishing a reflection axial potential at a remote end of the quadrupole mass filter, so as to turn the ions back and use the quadrupole mass filter to select a precursor ion in reciprocating filtering of the ions; resetting amplitude or frequency of a high frequency trapping voltage corresponding to the trapping mass-to-charge ratio range in the linear ion trap, and resetting axial potential distribution between the quadrupole mass filter and the linear ion trap, so that ions returning from the quadrupole mass filter to the linear ion trap are accelerated and collide with collision gas in the ion trap; and finally, setting DC potentials of front and rear end caps of the ion trap, so that product ions generated by collision dissociation in the mass-to-charge ratio range are captured by the ion trap.

The present invention further provides a new method to control the total amount of ions injected in an ion trap, which includes first obtaining a relation, that is, pre-detected mass spectrum, between ion strengths and mass-to-charge ratios generated by an ion source within a short time through a quadrupole mass filter and a linear ion trap only serving as a deflector, then calculating an ion injection time required when the ion trap reaches the optimal ion injection volume according to the total ion number of the pre-detected mass spectrum, controlling the total amount of the injected ions by changing the time when an ion gate in the front of the ion trap is at open potential, and applying a high-frequency and high-voltage signal to radial trapped electrodes of the ion trap, so that ions transmitted from the quadrupole mass filter can be sufficiently accepted and captured and the total amount thereof in the ion trap reaches the optimal value.

In sum, the instrument scheme according to the present invention can realize multi-stage tandem mass spectrometry (three stages or more), and also can realize higher product ion output efficiency through direct collision cracking in the ion trap, which has high sensitivity of full-spectrum scan of the linear ion trap and also can obtain broader dynamic ranges of first-stage mass spectra and second-stage mass spectra and broader mass-to-charge ratio ranges of product ions obtained through tandem mass spectrum collision dissociation with the quadrupole mass filter; moreover, the gas phase sample EI source fragment ion spectra obtained with the instrument can have mass spectrum retrieval library compatibility identical to that of the scan spectrogram of the conventional quadrupole mass filter. The instrument scheme retains unique advantages of respective ion mass analyzers while gathering advantages of a variety of mass spectrometers, and overcomes the shortcomings of the single quadrupole mass spectrometer or ion trap mass spectrometer.

BRIEF DESCRIPTION OF THE DRAWINGS

In order to make the objectives, features, and advantages of the present invention more comprehensible, a detailed description of the present invention is given below with reference to the accompanying drawings.

DETAILED DESCRIPTION OF THE INVENTION

Figure 1:
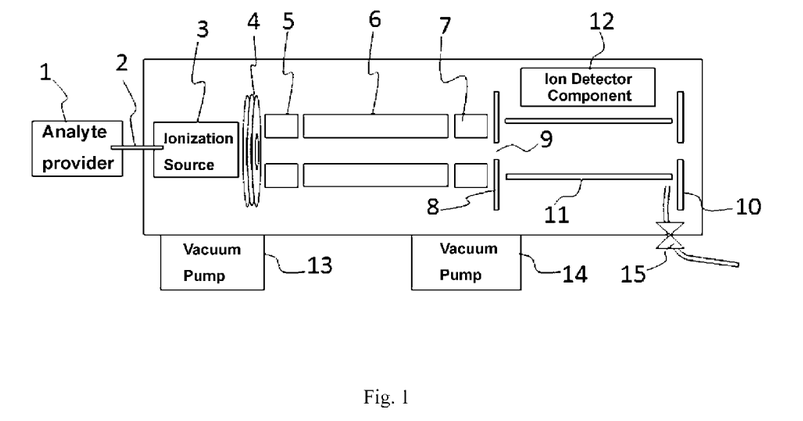
FIG. 1 is a structural diagram of a mass spectrometer with a quadrupole mass filter in tandem with a quadrupole linear ion trap.

FIG. 1 is a structural diagram of a mass spectrometer according to the present invention. A gas phase material under analysis is sent from a sample source 1 such as gas chromatograph to an ionization source 3, for example, an electron ionization source ionized externally, in a vacuum chamber through an air tight sample pipe interface 2. Ions are generated in the ion source and are educed from the ionization source, are focused through a set of single-hole lenses 4, and then fly into a downstream quadrupole rod system group. The quadrupole rod system group consists of three sections, namely, a pre-rod system 5, a main rod system 6, and a rear rod system 7, and can operate in two modes: ion guide mode and ion select mode. In the ion guide mode, quadrupole rod systems of all the sections are applied with identical pure radio frequency (RF) signals to generate a quadrupole field, and the quadrupole field has a strong radial focusing effect and can make ions in a broad mass-to-charge ratio range pass with relatively high kinetic energy. In the ion select mode, the pre-rod system and the rear rod system are only applied with pure RF signals and the main rod system is applied with a composite signal generating a DC quadrupole field to provide mass resolving DC voltage and RF voltage.

The so-called "provide mass resolving DC" in the composite signal makes the main rod system 6 generate DC quadrupole field components which have a selectively passing function for ions in a specified mass-to-charge ratio range; therefore, the main rod system is also called a quadrupole mass filter; and the pre-rod system only has a quadrupole field where RF signals are generated, which can reduce ion loss caused by a quadrupole edge field when ions enter from an axially symmetric lens system to the filter quadrupole field. The effect of the rear rod system is similar to that of the pre-rod system, that is, for transmitting ions undergoing the mass selection process. The section forms a pure RF edge field, in this way, ions in a particular mass-to-charge ratio may not be excited radially, and this is good for ion focusing, so that the ions can pass through a downstream linear ion trap space encircled and defined by a front ion gate 8, a rear ion gate 10, and a radially trapped electrode group 11 through a small hole 9 on the front ion gate 8, and the ion loss caused in the front ion gate and the ion trap space is reduced.

Afterwards, an ion detector module 12 is set at a side of the linear ion trap, configured to detect ions passing through the quadrupole mass filter and the linear ion trap. All the devices above are disposed in a vacuum chamber, and vacuum pumps 13 and 14 are used for vacuum extraction. The instrument may be provided with a valve piping 15 that imports collision gas in the linear ion trap from the outside of the vacuum chamber, so as to control and regulate collision pressure helping ion trapping or dissociation. The size of the small hole 9 on the front ion gate 8 also controls pressure ratio of the imported collision gas inside and outside the linear ion trap, and generally, to ensure a desired vacuum state of the quadrupole mass filter 6 and the ionization source 3, the diameter of the small hole 9 should not be too large, usually between 1 mm and 3 mm.

Figure 2:
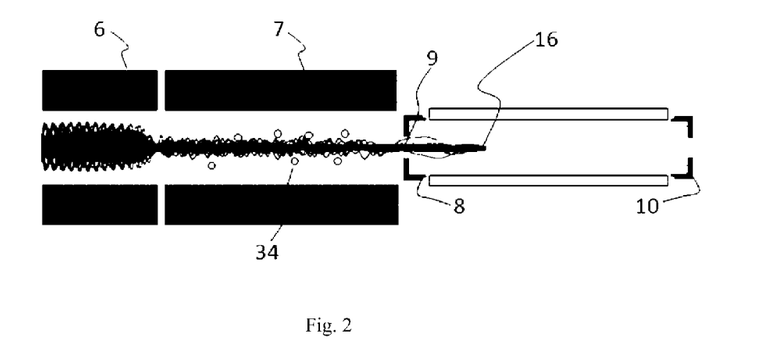
FIG. 2 is a schematic diagram of ion transmission trajectory in an ion optical system including a quadrupole mass filter with a rear short rod system and a linear ion trap.

The rear short rod system 7 in the instrument improves the ion trajectory educed by the quadrupole mass filter, as shown in FIG. 2, the quadrupole mass filter main rod 6 selects an ion current 16 having a particular mass-to-charge ratio, when the ion current passes through the rear rod system 7 applied with a pure RF voltage, divergence of the ion current 16 is inhibited after passing through the rear rod system 7 since the rear rod system 7 does not have a quadrupole electric field of the signal "providing mass resolving DC", so that main ion currents all can be injected into a linear ion trap space constrained by two ion gates 8 and 10 through the hole 9 on the front ion gate 8 of the linear ion trap.

The conventional instrument structure includes more than two linear ion traps, usually consisting of four columnar electrodes and two end cap electrodes. A hole is opened in the front end cap electrode centrally for ion introduction, and a slot is opened on at least one columnar electrode for ion extraction.

Figure 3:
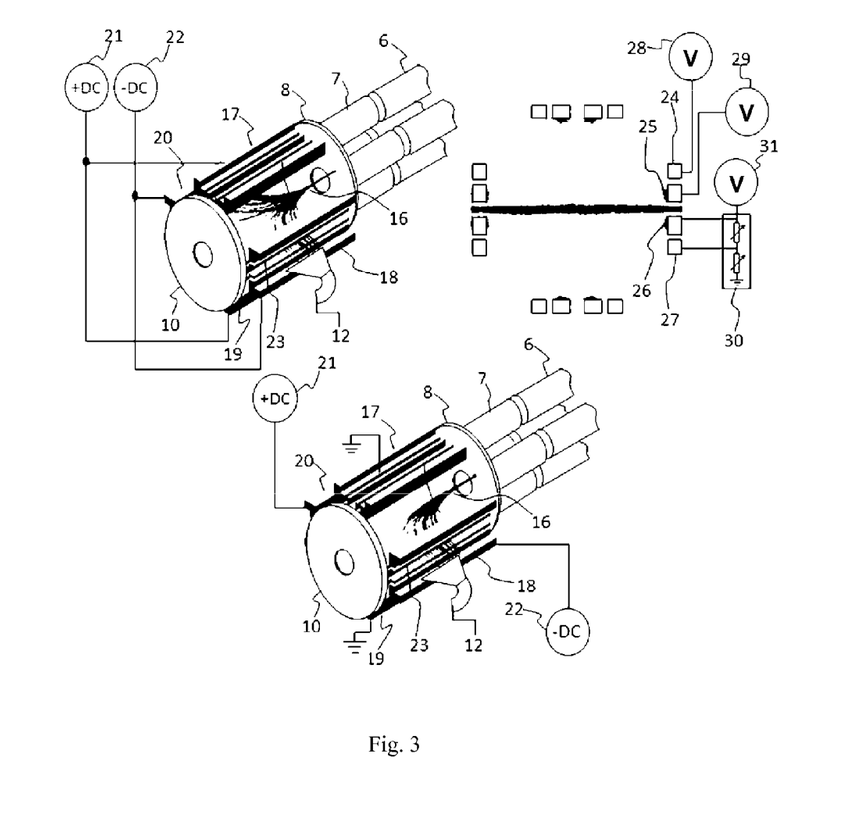
FIG. 3 is a structural schematic diagram of setting deflection DC voltages on electrodes to make the linear ion trap be an ion deflector.

Specifically, referring to FIG. 3, a linear ion trap in this embodiment may have the following structure; it includes two end cap ion gates 8 and 10 each having a hole opened thereon and four plane electrode groups 17, 18, 19, and 20 that are symmetrically distributed about a rotating shaft. Each plane electrode group consists of an insulator, for example, a ceramic block, whose surface is covered with a metal layer to form multiple discrete electrodes.

When the linear ion trap in the present invention serves as an ion storage device, a high-voltage high-frequency signal is applied to a set of opposite electrode groups 17 and 19, a high-voltage high-frequency signal whose phase is opposite to that on the electrode groups 17 and 19 is applied to the other set of opposite electrode groups 18 and 20, and the two voltage signals with opposite phases may form an alternating electric field mainly composed of a 2D alternating quadrupole electric field in the linear ion trap, so as to form a radial pseudopotential well for ions above a certain mass-to-charge ration to trap the ions radially. Meanwhile, for positive ions, potentials whose average potential is higher than that of the electrode groups 17, 18, 19, and 20 may be applied to the end cap ion gates 8 and 10, so as to complete axial trapping for the positive ions. For negative ions, potentials whose average potential is lower than that of the electrode groups 17, 18, 19, and 20 may be applied to the end cap ion gates 8 and 10, so as to complete axial trapping for the negative ions.

Since the ions may convert carried higher potential energy into kinetic energy when being injected from the outside of the trap, and in the case that it is necessary to trap the ions injected from the outside of the trap, to avoid that the ions deviate from the ion trap once more and to improve the trapping efficiency, it is often necessary to apply some special means to add potential well depth of the ion trap or remove the additional kinetic energy. A method for increasing an axial potential barrier of the ion trap includes: regulating a potential difference of the rear rod system 7 and the main rod system 6, modulating the ion current 16 passing through the main rod system 6 into a group of periodic ion pulses in the time dimension, and after each ion pulse is injected into the linear ion trap space, pulse-changing the potentials of the front and rear end cap of the ion trap to trap the ions before the ions are reflected to leave the ion trap.

Another effective method is introducing collision cooling gas when capturing ions, which is generally a substance of smaller molecular weight, for example, helium. Sample ions release excessive kinetic energy by colliding with gas molecules, so as to improve the trapping efficiency. In the case of gas chromatograph spectrometer, the collision cooling process can be completed with helium in carrier gas by regulating sample-carrier gas split ratio of a shunt. In the case that the collision cooling gas is insufficient, as shown in FIG. 1, the cooling gas is supplemented into the linear ion trap additionally through a collision cooling gas line and a regulating valve 15. The working mode of the gas line and the regulating valve 15 may be regulating flow continuously or introducing gas pulse.

The introduction of the collision cooling gas, in addition to enhancing the trapping efficiency of the linear ion trap alone, can reduce, through collision cooling, magnitude and intensity for the radial motion of the ions outside the instrument axis, that is, the so-called collision-focusing effect. Generally, in a mass spectrometer taking the quadrupole mass filter as a unique mass analyzer, since the space where the quadrupole mass filter locates has a so-called quadrupole field of signals "providing mass resolving DC", ion currents diverge seriously when flowing out of the quadrupole mass filter. In the mass spectrometer according to the present invention, as shown in FIG. 2, the rear rod system 7, in addition to regulating the ion current cross-section by using its own pure RF field, may also use collision cooling gas 34 flowing out of the linear ion trap to realize collision focusing in the rear quadrupole rod, so as to further enhance the focusing effect of the ion current 16, thereby increasing the total amount of the ions entering the ion trap and the overall trapping efficiency.

By comparing with the structure of the mass spectrometer taking the quadrupole mass filter as a unique mass analyzer, since the total length of the quadrupole mass analyzer and its front and rear rods is generally about 150-300 mm, it may function as an efficient ion guide and effective gas pressure differential transition structure between ion sources requiring high vacuum conditions and the linear ion trap requiring a certain collision gas pressure. Therefore, when the ion optical system of the instrument in the present invention and an ion optical system directly connected to an ionization source linear ion trap analyzer have similar ion transmission and trapping efficiency, the instrument in the present invention has lower background pressure at the ion source. This is good for prolonging the life of the ion source and its filament, and can tolerate a larger sample source carrier gas flow.

As stated above, when an ion trap-type mass analyzer realizes its mass analysis function, ions usually need to go through hundreds of microseconds to tens of milliseconds for capture storage, collision cooling, and mass-to-charge ratio scan. During this period of time, various dissociation processes exist in the ions. For some abundance spectra relying on the ionization source to dissociate fragment ions or a specific short-lived ion monitoring mode analysis method, for example, the most common method, in the field of gas chromatography-mass spectrometry applications, of using the ion abundance spectrum generated by electron bombardment ionization source ionization source to make qualitative analysis of the gas chromatographic peak effluence, the above process may damage the ion abundance ratio directly generated by the ionization source, thereby causing a problem that it is difficult or even unable to comparatively look up the mass spectra collected from the ion trap, from a standard library obtained from the mass analyzer with shorter ion residence time such as the conventional magnetic fan deflection mass spectrometry and quadrupole mass spectrometry. This greatly limits the applications of the mass spectrometer taking the ion trap as mass analyzer.

By directly combing the pre-mass analyzer having shorter ion residence time, such as magnetic sector deflection or quadrupole rod, with the ion trap, the mass spectra with no abundance change in the analyzer obtained through mass analysis performed by the pre-mass analyzer can be directly used to perform the spectra comparative lookup. However, when the linear ion trap does not serve as the mass analyzer, the ions injected into the linear ion trap axially cannot be ejected from a specified radial direction. So, the present invention provides a method for switching a linear ion trap into an ion beam deflector, including: as shown in the left diagram of FIG. 3, applying a forward bias DC voltage to electrode plates 17 and 19 through a DC power supply 21, and applying a negative bias DC voltage to electrode plates 18 and 20 through a DC power supply 22, thereby generating an electrostatic quadrupole deflection electric field, so that positive ion currents injected into the trap are ejected from the electrode plates 18 and 20 through an exit 23, so as to be detected by an ion detector 12 located at the side. When it is necessary to detect negative ions, polarity of the power supply 21 and 22 requires to be changed. Since the ion currents do not go through a long motion in the trap, the influence of its chemical stability on the ion abundance of the spectrum obtained by the quadrupole analyzer 6 can be ignored.

In the case of using only one lateral ion detector, another method for forming a dipole deflection electric field in a trap may be used. As shown in FIG. 3, for positive ion currents, a positive deflection DC voltage may be applied to an electrode plate 21 through a DC power supply 21, a negative deflection voltage is applied to an electrode plate 18 through a DC power supply 22, and electrode plates 17 and 19 may be grounded or applied with a potential with lower amplitude so as to maintain balance or obtain an appropriate field axis potential, so that an electrostatic dipole deflection electric field is generated in the trap radially, and the positive ion currents injected into the trap pass through the exit 23 at the side of the electrode plate 18, so as to be detected by an ion detector 12 at the side of the electrode plate 18.

Generation of the effective deflection electric field in the linear ion trap is not limited to the above two basic field structures, and to improve expelling efficiency, an additional DC bias field or high-order multi-polar electric field components may be applied to the electric field. As shown in the right diagram of FIG. 3, a method includes: replacing a single electrode plate 18 with multiple striped discrete electrodes such as 24, 25, 26, and 27, and only applying a deflection auxiliary voltage to the discrete electrodes 25 and 26 near the side exit so as to provide an electric field with stronger focus force near the side exit to improve the ion ejection status. Alternatively, a method of simultaneously applying a bias voltage opposite to that of the electrode strips 25 and 26 near the exit to discrete electrodes 24 and 27 away from the exit may be used to further improve the directivity of the deflection ions. Voltages of the discrete electrodes 24, 25, 26, and 27 may be controlled by a discrete power supply such as 28 and 29, or be allocated from the same power supply 31 by a divider resistance network 30.

Additionally, to improve the situation that the electrostatic deflection electric field may has mass discrimination for the deflection ejection efficiency of ions with different mass-to-charge ratios, in actual applications of the present patent, amplitude of the deflection field, DC bias or multi-polar field components can be modified along with synchronous scan of a mass select window center value of the quadrupole mass filter 6, so as to eliminate or compensate for the ejection efficiency discrimination effects.

Compared with the working mode that the instrument only including a single quadrupole mass filter only selects one class of ions in a specific mass-to-charge ratio and loses all the remaining ions, another characteristic of the present invention is that the combination of the quadrupole mass filter and the linear ion trap may use almost all the ions generated by the ionization source to form mass spectrometry signals, so as to enhance sensitivity and detection limit capability of the instrument.

The method specifically includes: removing the so-called signals "providing mass resolving DC" applied to the quadrupole mass filter 6, and at this time, when entering the quadrupole mass filter 6, all the ions whose mass-to-charge ratio is greater than a specific value are only affected by radial pseudopotential generated by a high-frequency high-voltage signal applied to the quadrupole mass filter 6, are trapped in a columnar region near the axis of the quadrupole mass filter to move along the axis, and enter the linear ion trap through the rear modulation rod 7. The specific value is called the minimum passing mass of the quadrupole mass filter, and the quadrupole mass filter of a particular size is only associated with the amplitude and frequency of the high-frequency high-voltage signal applied thereto.

The linear ion trap applies a high-frequency trapping voltage to one set or two sets of orthogonal radial trapped electrode groups such as 17, 19 and 18, 20 and captures the ions with different mass-to-charge ratios from the ion source. Then, the linear ion trap scans the trapping high-frequency high-voltage amplitude or frequency or a combination thereof, to change the so-called secular vibration frequency of the ions in the trap, that is, the feature frequency relating to the ion mass of the ions in the radial periodic motion in the linear ion trap, resonates the ions with the frequency of a pair of or one low-frequency auxiliary excitation voltage(s), for example, dipole excitation voltage, coupled on the radial trapped electrode group in an order of mass-to-charge ratios, so that the ions in the ion trap are selectively expelled to the detector according to the mass-to-charge ratio, thereby forming a mass spectrum. In the case that the trap has a high pole field with more than four poles, the indicators such as mass resolution and chemical shift of the spectra results may be improved by using nonlinear resonance ejection phenomena formed by the high pole field and dipole excitation. In addition to the dipole excitation, the auxiliary excitation voltage also indicates any combination for forming a quadrupole excitation electric field or other multi-pole excitation electric field or multiple multi-polar (including dipole) excitation electric fields, so as to resonate with the secular vibration frequency of the ions, and increase the trajectory amplitude of the ions and the alternating voltage signal of the kinetic energy.

In the case of monitoring multiple product ions from the same precursor ion, the linear ion trap does not need to switch to multiple channels like the triple quadrupole mass spectrometer, but only needs one scan; therefore, the unit time of such multi-channel ion reaction monitoring can be enhanced to monitor the reaction speed, which helps the co-eluting analysis of complex mixtures.

Figure 4:
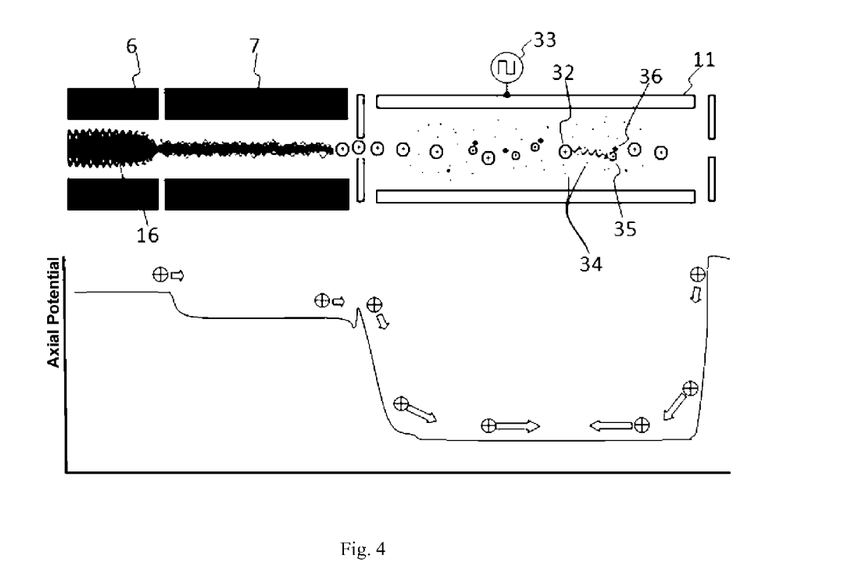
FIG. 4 is a schematic diagram of accelerating precursor ions isolated by the quadrupole mass filter to be introduced into the inflatable ion trap and collision dissociation of the precursor ions therein.

In the case that the quadrupole mass filter operates in the ion mass select mode, the instrument structure according to the present invention can make precursor ion selection from sample ions through the quadrupole mass filter, realizes high-energy collision dissociation, and scan the linear ion trap to collect a product ion spectrum of the ion in a specific mass-to-charge ratio, that is, a second-stage mass spectrum. Specifically, for a positive ion mode, in the ion introduction process, referring to FIG. 4, the ion current 16 including various sample ions first passes through the quadrupole mass filter 6 and is filtered to be an ion current that only includes a precursor ion 32 in the selected mass-to-charge ratio, and passes through the rear rod system 7. At this time, a trapped high-frequency high-voltage 33 is applied to a radial trapped electrode group 11 of the linear ion trap, DC bias of the quadrupole mass filter 6 and the rear rod system 7 is regulated, so that the DC bias is about 20-40 V higher than that of the linear ion trap, collision gas of larger molecular weight, for example, helium, is introduced in the linear ion trap, and ions injected into the linear ion trap may obtain 20-40 eV kinetic energy due to the original electric potential energy conversion. After the ions with such high energy collide with collision gas molecules 34, a larger portion in its kinetic energy is converted to internal energy of the ions, which finally breaks and dissociates weak chemical bonds in the ions. A part of kinetic energy of the dissociated product ion 35 may be lost through loss of a neutral section 36; therefore, the product ion 35 has insufficient energy to leave axial potential well of the linear ion trap, and the collision cooling may also accelerate the process. In a negative ion mode, the potential change of the concerned electrodes is opposite to that of the positive ions. Since the collision energy of the ions is higher in this mode, the dissociation speed is faster, and the mass of the precursor ion to be dissociated may be far greater than the lower mass limit in the ion trap injection stage, the so-called one third lower mass limit easily occurring in resonance-induced dissociation used in the ion trap-type instrument does not exist.

In addition to the method for filtering other ions with a quadrupole mass filter disposed externally, the linear ion trap itself also can be used to make ion selection for ions trapped in the trap, and the specific method includes coupling a pair of auxiliary excitation alternating excitation signals or applying an auxiliary excitation alternating excitation signal to the radial trapped electrodes in the linear ion trap, trapping high-frequency high-voltage signals through twice scan, so that the secular vibration frequencies of all the ions greater than the selected mass range ascend in sequence to make the ions pass through a resonance excitation band decided by the alternating excitation signal and ejected, and the secular vibration frequencies of all the ions less than the selected mass range descend in sequence to make the ions pass through a resonance excitation band decided by a dipole alternating excitation signal and ejected so as to isolate ions in the selected mass range; or applying an auxiliary excitation composite signal sequence in continuous frequency domains, and introducing a small-range frequency Notch in the frequency domains, so as to resonantly eject and exclude ions greater or less than the selected mass; or imitating the method of the quadrupole mass filter principle, attaching a signal providing mass resolving DC to the high-frequency high-voltage signal applied to the radial trapped electrodes of the linear ion trap, and modulating a and q values of the ions located above the stability diagram, so that unwanted ions are removed by making high mass limit and low mass limit co-exist in the ion mass-to-charge ratio range stored in the ion trap, in which a is quadrupole DC signal amplitude related dimensionless quantity, and q is quadrupole high-frequency signal amplitude related dimensionless quantity.

Figure 5:
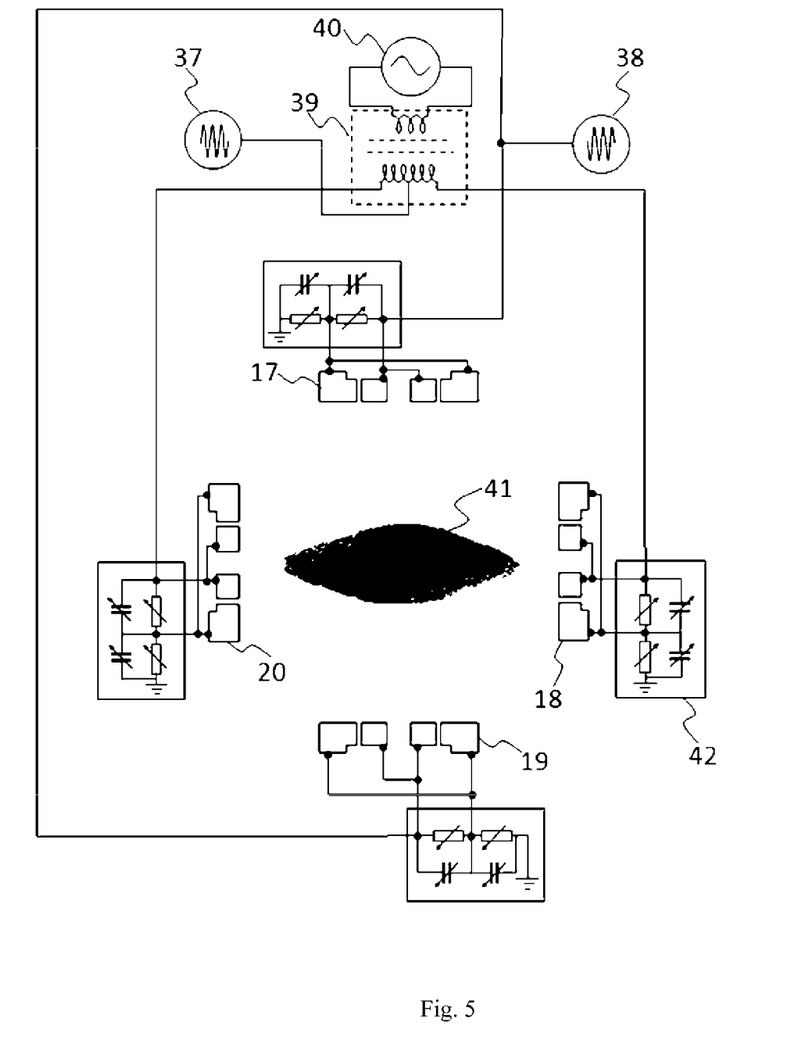
FIG. 5 is a structural schematic diagram of precursor ions isolated by the quadrupole mass filter realizing a resonance excitation collision dissociation process in the ion trap.

The instrument according to the present invention also can realize the resonance-induced dissociation technology used in the common ion trap-type instrument, dissociate ions trapped in the ion trap or specified ions selected through the above scheme, and obtain second-state and third-stage tandem mass spectra, and fourth-state and fifth-stage tandem mass spectra as well as instrument sensitivity and any multi-stage tandem mass spectrometry allowed by operation loss can be obtained by repeating the selection process and the dissociation process. The specific manner of the CID technology is: as shown in the linear ion trap cross-section in FIG. 5, applying a high-frequency high-voltage signal generated by voltage source devices 37 and 38 to one set or two sets of orthogonal radial trapped electrode groups such as 17, 19 and 18, 20, changing the trapping high-frequency high-voltage amplitude or frequency or a combination thereof, so that the secular vibration frequency of the ions to be dissociated in the trap is close to the frequency of a pair of or one low-frequency dipole excitation voltage(s) 40 coupled to the radial trapped electrode groups through a coupling device, for example, a transformer 39, thereby increasing vibration amplitude and average kinetic energy in the excitation direction, as shown by an ion trajectory cloud 41. The excited ions collide with the collision gas of larger molecular weight introduced in the ion trap, so that kinetic energy thereof is converted to internal energy, thereby completing the fragmentation process.

The resonance-induced dissociation technology may also be used to further improve the dissociation efficiency through radial excitation when injecting ions into the ion trap from the quadrupole mass filter to perform axial collision dissociation. Besides, since the frequency required by radial resonance-induced dissociation is associated with the excited ions, interference of product ions generated by other precursor ions produced due to molecule-ion reaction may be excluded while the selected ions are excited.

The resonance-induced dissociation technology may combine with the high-energy axial collision technology to perform mixed dissociation method tandem mass spectrometry, for example, selecting a precursor ion once with a quadrupole rod, obtaining the second generation precursor ion trapped in the trap through axial collision dissociation during capture of the ion trap, and according to the selective auxiliary resonance excitation method stated above, or a similar method of selecting ions by regulating a and q values of the ions in the stability diagram with a quadrupole mass filter, removing unwanted ions according to a mass-to-charge ratio, and retaining ions in a certain mass-to-charge ratio for continuous cracking, so as to select the second generation precursor ion of specific mass.

Then, the resonance-induced dissociation method is used to dissociate the second generation precursor ion of specific mass to obtain the second generation product ions, and scan the trapped high-frequency high-voltage of the ion trap to selectively expel the product ions in the ion trap in an order of mass-to-charge ratios to the detector, so as to form third-stage tandem mass spectra. The ions of specified mass may be expelled separately and selectively to complete third-stage tandem select ion monitoring. In common with the technology of generally obtaining first-stage and second-stage tandem mass spectra in a single linear ion trap, resonant dipole excitation may also be used for finally expelling ions to obtain a mass spectrum in the mixed dissociation tandem mass spectrometry, so as to cooperate with auxiliary excitation technical means such as nonlinear dipole excitation and quadrupole excitation of ion trap high pole field components to enhance the spectra quality of the ultimate mass spectra.

In the case of having special requirements for single spectral sampling time, the ion select technology and the dissociation technology can be applied together on condition that specific implementations are not in conflict, so as to form a second-stage tandem mass spectrum continuous analysis model. For example, in the realization of precursor ion high-energy axial collision dissociation, a dipole excitation signal corresponding to the secular vibration frequency of the product ions in a particular mass-to-charge ratio and a dipole excitation signal corresponding to a continuous frequency domain of the frequency notch are respectively applied to two sets of electrodes 17, 19, and 18, 20 in different directions in the radial trapped electrode groups of the linear ion trap, which can detect continuous product ion current signals from one side of the excitation signal applied corresponding to the secular vibration frequency of the product ions in the case of continuous injection of precursor ion currents. Other ions are expelled from another radial direction through the dipole excitation signal in the continuous frequency domain, avoiding saturation of the linear ion trap. Especially after a radial distribution high-order multi-pole field is introduced to the linear ion trap by correcting the geometrical structure or using a voltage attenuation network distributor 42 to generate voltage distribution, the effect of the excite-select ion working mode may be further improved by using field asymmetry of the high-order multi-pole field such as octupole field and hexadecapole field in two or more directions and a correspondence relation of mass-to-charge ratio scan directions with fast nonlinear excitation performance in the directions.

It should be noted that, when the linear ion trap in this embodiment is a digital ion trap driven by a switching voltage, since a high-voltage electronic switch can switch to work at any time in any cycle above sub-microsecond to hours level, it has a number of advantages in operation involved in rapid or substantial changes of the operating mass-to-charge ratio. Meanwhile, unlike that the conventional ion trap uses an inductor-capacitor resonant circuit to realize RF high-voltage sine wave trapped signals, owing to arbitrariness of changeover of the electronic switch, the RF high voltage in the digital ion trap can realize phase discontinuous change, which provides a realizing method for some working modes that cannot be realized in the conventional ion trap, such as performing ion trap and dissociation in non-stable areas or obtaining low-mass product ions in the resonance excitation collision dissociation technology.

By taking the method for obtaining low-mass product ions in the resonance excitation collision dissociation technology as an example, due to the time arbitrariness of the switch changeover in the digital ion trap, several long-cycle square wave sequences with one to multiple cycles may be inserted at intervals to a short-cycle square wave sequence corresponding to the ultra-low low mass limit, since the pseudo-potential well where the ions locate is deeper for the long-cycle square wave sequences, the precursor ion can obtain enough kinetic energy in the case of dipole excitation, the ions having high kinetic energy can react with collision gas around the ions and convert part of the kinetic energy to its internal energy, and when the internal energy accumulates to some extent, there is chance of fragmentation for the precursor ion. Since only multiple long-cycle square waves are applied, although the ion trajectory of the product ions of ultra-low mass is unstable in the trapping of the long-cycle square waves, it is insufficient to leave the ion trap due to short time, the product ions of ultra-low mass can be obtained after the long-cycle square waves end. In the common sine wave ion trap, the method cannot quickly jump due to the magnitude change of the since wave, making it difficult to retain the product ions of ultra-low mass while dissociating the precursor ion.

However, even if the ultra-fast frequency hopping technology is used, for the product ions outside the stable region of the ion trap in resonance excitation dissociation of the precursor ion, the intensity on the ultimate product ion spectrum still declines significantly. With respect to the cracking efficiency of the tandem mass spectrum with more than two stages, especially the problem of the generation efficiency of the product ions of low mass, the present invention provides a new method for performing mass filtering and dissociation on ions trapped in a linear ion trap with a quadrupole mass filter by combining the linear ion trap with the quadrupole mass filter.

Figure 6:
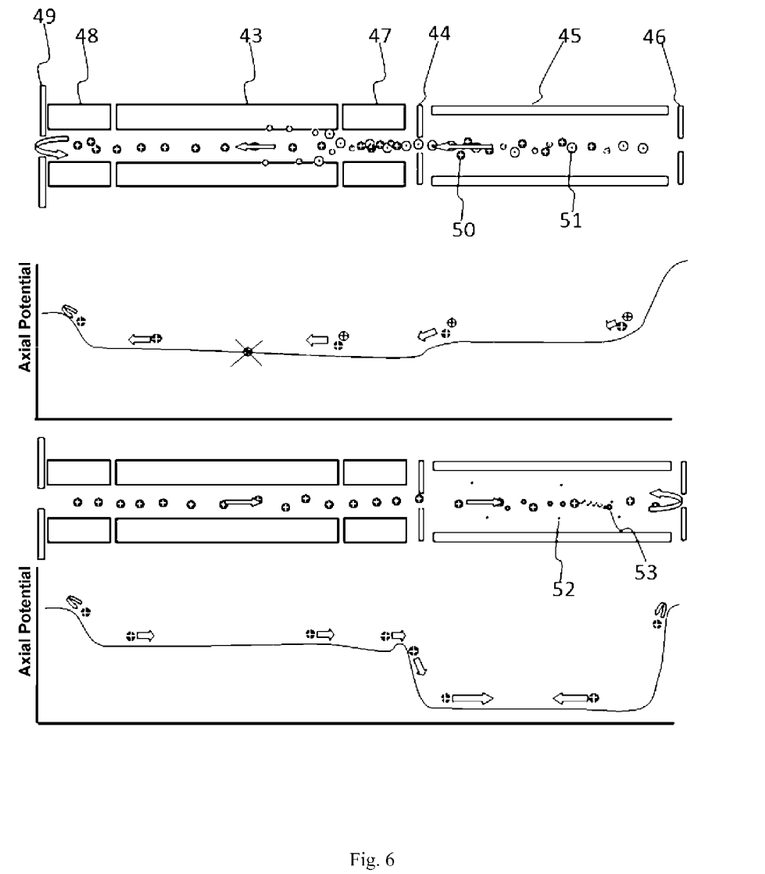
FIG. 6 is a schematic diagram of ions captured in the linear ion trap making mass selection and accelerating collision dissociation through a quadrupole rod in tandem therewith.

Specifically, referring to FIG. 6, when ions having analysis requirements, such as original ions or ions of selected mass injected from an ion source through an ion source interface or an ion guide optical system, or ions captured in an ion trap, or product ions of the ions after collision dissociation, are captured in the ion trap, a quadrupole mass filter main rod 43 in tandem therewith is provided with a high-frequency high-voltage and a DC voltage signal having mass resolution, making it in the working state of selecting and passing through a next precursor ion 50. Afterwards, an accelerating expelling electric field along the axial direction is generated in the ion trap by pulse-changing DC potential bias of one, two, or three of an ion gate 44, a radial trapped electrode group 45, and a rear ion gate 46 where the linear ion trap approaches one side of the quadrupole mass filter according to polarity of the selected precursor ion 50. Ions in the ion trap may reversely flow in the front quadrupole mass filter 43 through the pre-rod 47 nearby, at this time, potentials higher or lower than the quadrupole mass filter main rod may be set on a pre-rod 48 at a remote side of the quadrupole mass filter or an electrode 49 at a remote exit thereof according to the polarity of the precursor ion 50, so that the ions turn back through the quadrupole mass filter, and go back to the ion trap through the quadrupole mass filter again, ions 51 except the next precursor ion 50 allowed passing are excluded by the quadrupole mass filter completely now, the process is usually about tens of microseconds, in this process, the voltage or frequency of the high-frequency high-voltage on the radial trapped electrode 45 is changed for modifying the mass-to-charge ratio range of the captured ions in the linear ion trap, so as to cover the mass-to-charge ratio range of the minimum product ions possibly generated, and field axis potential distribution of the trap is reset by changing potentials of ion gates 44 and 46 at two ends of the linear ion trap, to determine the axial kinetic energy possessed by the precursor ion 50 after reentering the ion trap. Since the mass-to-charge ratio of the next precursor ion 50 and the time intensity of pushing pulse axially by the ion trap have been decided in the operations above, the time for the precursor ion 50 going back to the ion trap to leave the ion trap once more can be obtained. Before the time point, the precursor ion 50 will be captured by changing potentials of the ion gates at two sides of the linear ion trap to stop the precursor ion 50 from leaving.

Meanwhile, if the precursor ion 50 has certain kinetic energy when going back to the ion trap, the precursor ion 50 can collide with collision gas 52 introduced into the ion trap to obtain a product ion 53, and a product ion mass spectrum may be further obtained.

The advantage of the method lies in that, either ions previously stored in the linear ion trap or ions generated by cracking in the linear ion trap can be fragmented by means of high-energy axial collision dissociation, without relying on the limit of the radial trapped potential well of the linear ion trap, thus avoiding the problem of the product ion lower mass limit in the ion trap tandem mass spectrum. This provides a solution for realizing real no low-mass loss of third-stage or more tandem mass spectrum in the system for a quadrupole mass filter in tandem with a linear ion trap involved in the present invention.

The application range of the method is not limited to a quadrupole mass filter-linear ion trap tandem mass spectrometer, which may also be applied to a linear ion trap-quadrupole mass filter (that is, the quadrupole mass filter is located downstream of the ion trap) tandem mass spectrometer. For example, in the triple quadrupole mass spectrometer commonly used at present, the mass spectrometry process can also be performed according to the method to use a collision chamber as the linear ion trap and apply a reflective voltage to an end of one of the front and rear analyzing rods, to obtain a tandem mass spectrum with more than two stages.

It should be noted that, to reduce the ion trap-quadrupole rod cross-contamination possibly existing in the method and further improve the extraction efficiency of the method, before ions stored in the ion trap are pulse-extracting, most of other ions are excluded by first using mass isolation means in a broader range, including the selective dipole resonance excitation method, or introducing quadrupole DC signals having mass selection force, the selection precursor ion is compressed simultaneously or then with the method of improving rear DC potentials of the linear ion trap. Meanwhile, before the precursor ion is filtered with the quadrupole rod, a high quadrupole DC pulse should be applied to the quadrupole rod temporarily to remove interference species with the same mass-to-charge ratio entering from the ion source; and in the precursor ion reciprocating analysis, a high blocking potential is applied to a focusing lens at the exit of the ion source to avoid the possibility that a next effluent ion interferes with the precursor ion and the product ions thereof.

It should be noted that, if it is unnecessary to make mass screening for ions temporarily expelled out of the linear ion trap in this process, but it is only wanted to make the high-energy axial collision dissociation for the ions screened in the ion trap, the quadrupole rod in the method may also be replaced with octopole, hexapole and other multi-pole ion guide devices, or ion funnel stack RF ring array guide devices, or a static reflection lens, and even another ion temporary storage devices such as high-pressure collision chamber and linear ion trap. As long as the ion guide or temporary ion storage devices can effectively save the ions ejected from the ion trap in the method for a period of time, return the ejected ions to the linear ion trap, and make a sufficient acceleration voltage difference exist between the ion guide and the ion trap in returning, the ejected ions returned can produce high-energy fragmentation dissociation in an ion trap with a relatively high background pressure and capture product ions.

Additionally, in the case of continuous ion sources, to avoid the situation that newly-injected ions interfere with spectra when the high-frequency high-voltage is scanned to obtain a mass spectrum, after the ions are introduced in the ion trap, and before ending the mass spectrum scanning and emptying the ion trap, the potential of the front ion gate of the linear ion trap needs to be raised or reduced to close ion injection. In this way, in a mass spectrometer including an ordinary single ion trap mass analyzer, ions generated by the ion source from ion introduction to next ion extraction may suffer loss.

In the instrument according to the present invention, if it is necessary to enhance sample detection limit or sensitivity is required, such loss can be further avoided through the structural features described. By taking FIG. 1 as an example, the specific method is: for the positive ion mode, after the final ion injection for the ion trap in any analysis method above ends and the potential of the front ion gate of the linear ion trap is raised, decreasing the DC bias of the rear rod system 7 to 1-20 V lower than that of the quadrupole mass filter 6. In this way, since the rear rod system is close to the linear ion trap, and the internal pressure is higher, collision cooling for ions injected into the rear rod system 7 can be realized, so that the ions passing through the quadrupole mass filter in the linear ion trap non-injection time can be buffered in the rear rod system 7. Before entering the next analysis cycle of the original first ion injection stage, the DC potential of the rear rod system 7 is pulse-increased and the potential of the front ion gate 8 of the ion trap is reduced to complete pulse injection of the ions. In the negative ion mode, the potential changes of the electrodes concerned are opposite to those of the positive ions.

Another problem existing in the ion trap-type mass spectrometer is that the highest storage capacity of the ion trap limits the analysis the dynamic range of sample concentration. In the linear ion trap, the highest ion storage capacity has been increased greatly as compared with the 3D ion trap. However, for the field of gas chromatography analysis, the outflow peak concentration may vary greatly. To solve this problem, an automatic gain control (AGC) method for controlling the amount of samples injected into the ion trap is introduced in the conventional ion trap mass spectrometer. To obtain appropriate injection volume or injection time, the ion trap and the following linear ion traps all need to add an extra short capture-scan stage in addition to formally capturing an ion scan cycle to trap a batch of ions for ion flow analysis. Such means first reduces the effective working time of the instrument, because the total amount of the injected ions in the short scan stage is not determined, the scan speed is fast, resulting in that the obtained spectra quality is bad, which cannot be used to improve data signal-to-noise ratio with the subsequent formal superposition, but only to estimate the total ion flow with its whole mass spectrum peak intensity; secondly, since the ion trap can only effectively capture ions in a certain mass-to-charge ratio range under the same condition, the so-called total ion current intensity obtained with ion trap pre-scan spectra is only the total ion current intensity in the mass-to-charge ratio range. This results in that, when uncertain samples are analyzed and in the case that the preset test trapping range and the actual outflow peak ion mass-to-charge ratio range are inconsistent with each other, the ion trap is still saturated since the total ion current intensity is underestimated. For the situation that a small number of samples whose ion mass-to-charge ratio deviates from the preset test trapping range and a large number of samples generating ions in the preset test trapping range jointly flow, since the ion injection time is decided by the injection flow of a large number of interfering substances, a small number of samples are insufficient, resulting in deterioration of the sensitivity of the small number of samples.

The present invention provides a new method for controlling the total amount of ions injected into an ion trap, which specifically includes: applying high-frequency and DC voltages with quick scan amplitude to the quadrupole mass filter, wherein at this time, the gating mass of the quadrupole mass filter varies rapidly with time, and applying an appropriate deflection voltage to radial trapped electrodes of the ion trap, or making it pass through the linear ion trap directly, so that ion currents varying with time can be detected on the following ion detector, which correspond to the relation between ion strengths in various mass-to-charge ratios generated by the ion source and the mass-to-charge ratios, namely, the pre-detected mass spectrum.

After the pre-detected mass spectrum is obtained, due to the continuity of the sample injection volume, continuous injection and ion currents within a short time such as tens of milliseconds under normal chromatographic conditions, including the ion types and the corresponding abundance, should not change dramatically; therefore, the ion injection time required when the ion trap reaches the optimal ion injection volume can be calculated according to the total ion number. Ions transmitted from the quadrupole mass filter can be fully accepted and captured according to the ion trap injection time calculated by changing the time when an ion gate in the front of the ion trap is at open potential and applying a high-frequency and high-voltage signal to radial trapped electrodes of the ion trap.

After the ions with the appropriate injection volume are captured, the radial trapped high-frequency high-voltage applied to the ion trap can be scanned by adding dipole resonance excitation or another multi-pole excitation alternating electric field in the trap, so that the ions in the ion trap can excite-resonate with the alternating field in an order of mass-to-charge ratios, making the ions selectively expelled from the outlet to the detector radially, so as to form a main detection mass spectrum. By integrating the main detection mass spectrum and the pre-detected mass spectrum as well as the total injection time, the mass spectrometer can restore total ion chromatogram (TIC) and selected ion chromatograms (XIC) of the samples injected in the ion source by calculating through software total ion volume and ion mass-to-charge ratios as well as the relative abundance accumulated in the unit time when the mass analyzer is always working theoretically. Since the total volume of the ions injected into the ion trap is controlled, the situation that the space charge effect and molecule-ion reaction of the ions in the ion trap cause mass displacement and resolution reduction can be suppressed, the method can obtain high-quality spectra and the selected ion chromatograms, which avoids the saturation of the ion trap and increases the largest analysis sample concentration. Meanwhile, since the main analysis process can be completed with the ion trap, almost all the ions in the main analysis stage can be used to obtain the mass spectra, thus avoiding the loss and waste of other ions except the ions in the positively selected mass-to-charge ratio when using the quadrupole rod to scan and obtain the full spectrum; so, the total ion sensitivity and detection limit may almost be equal to the quadrupole selected mass monitoring mode (SIM).

In some analysis schemes that need to obtain effluent mass spectral information and mass information and have high quantitative detection limit requirements for some specific substances, mass spectral information of the pre-detected mass spectrum can be used to further improve the analysis capability of the method for the samples. Specifically, only allow the samples to determine ions near the mass-to-charge ratio to obtain a pre-detected mass spectrum through a quadrupole mass filter and a linear ion trap operating in a deflection mode. Meanwhile, calculate the ion injection time required when the ion trap capture the optimal ion amount according to the ion number in a mass-to-charge ratio corresponding to the substance according to the pre-detected mass spectrum. Then, by changing the time when an ion gate in the front of the ion trap is at open potential according to the injection time and applying a high-frequency high-voltage signal most suitable for the mass-to-charge ratio corresponding to the ions to the radial trapped electrodes in the ion trap, the ions transmitted from the quadrupole mass filter can be accepted and captured with highest efficiency. Afterwards, spectrum scan is performed on ions stored in the ion trap to obtain a mass spectrum, so that the substance selected chromatographic signal of high sensitivity can be obtained. Since the method does not need to adjust the quadrupole rod to a high-resolution low-pass rate state sufficiently separating isotopes, in the case that the ion trap has no storage and ejection loss, the sensitivity and detection limit thereof even may be higher than the corresponding result of the quadrupole selected mass monitoring mode with the unit mass resolution. Isotope peak abundance information of the substance may also be obtained, further enhancing the chromatography and mass spectrometry data qualitative and quantitative accuracy.

The above method may also be used to control the quadrupole rod to select the precursor ion and use the ion number control in the tandem mass spectrometry using axial collision dissociation so as to avoid the saturation of the precursor ion and product ions generated through collision in the ion trap. A specific instance is provided as follows.

Before the quadrupole rod selects the precursor ions to high-energy inject the ion into the linear ion trap, first set the RF voltage amplitude and DC amplitude applied to the quadrupole mass filter, obtain a precursor ion selection range identical to that injected in the ion trap subsequently, and place the ion trap in the deflection mode and measure the ion strength passing through the quadrupole rod now so as to predict the total ion volume of the selected precursor ions in the unit time; then, apply a high-frequency trapping voltage to the electrodes of the linear ion trap, set the voltage in amplitude or frequency corresponding to a trapping mass-to-charge ratio, and set an axial potential difference between the quadrupole mass filter and the linear ion trap, so as to accelerate ions transmitted from the quadrupole mass filter and to collide with collision gas in the ion trap; store and fragment the ratio of the optimal number of the precursor ions according to the prediction ion strength signal and ion trap energy measured previously, and calculate and set a duration, so that ions in the selected mass-to-charge ratio passing through the quadrupole mass filter only in this period of time are accelerated and enter the ion trap, and collide with the collision gas in the ion trap; when exceeding the time, close the ion gate. Set DC potentials of the front and rear end caps of the ion trap, so that product ions in the above mass-to-charge ratio range generated through collision dissociation are captured by the ion trap, and then perform spectrum scan on the captured ions to obtain a tandem mass spectrum.

The device for a quadrupole mass filter in tandem with a linear ion trap according to the present invention can also be used to perform a number of unlisted operation methods or compound methods of the above listed operation methods, which are not listed one by one herein, but the scope of the present invention is defined by the claims.

What is claimed is:

1. A mass spectrometer, comprising:
   an ion source in a vacuum environment for ionizing gaseous or vaporized samples by means of electron impact or ion reaction;
   a quadrupole mass filter located downstream of the ion source;
   a straight linear quadrupole ion trap located downstream of the mass filter, having a set of field forming electrodes around an longitudinal axis of the straight linear quadrupole ion trap and at least one sideway outlet, wherein the straight linear quadrupole ion trap is the only one ion trap of the mass spectrometer;
   at least a switchable voltage source device configured to switchably generate a trapping high frequency voltage or a deflection voltage applied to the electrodes to form an electric field in the straight linear quadrupole ion trap, wherein at least in part of the operation time of the straight linear quadrupole trap, the switchable voltage source device delivers voltages to generate a radial deflection field in the straight linear quadrupole ion trap, and the radial deflection field causes ions selected by the quadrupole mass filter for their mass to charge ratio and entering the straight linear quadrupole ion trap to be continuously deflected towards the sideway outlet, thereby temporally convert the straight linear quadrupole ion trap as a continuous ion bender which expel the selected ions radially out through the sideway outlet without being accumulated or without mass-selective treating in the straight linear quadrupole ion trap; and
   an ion detector disposed at a sideway of the straight linear quadrupole ion trap, configured to continuously receive and be impinged by the ions extracted from the sideway outlet of the straight linear quadrupole ion trap.

2. The mass spectrometer according to claim 1, wherein the quadrupole mass filter comprises a rear short rod system, and an end cap of the straight linear quadrupole ion trap in conjunction with the rear short rod system has an ion entrance.

3. The mass spectrometer according to claim 1, further comprising a pulse gas providing device, configured to provide required cooling gas and collision gas for the straight linear quadrupole ion trap, and stop the cooling and collision gas when the electric field in the straight linear quadrupole ion trap is switched to deflection field.

4. The mass spectrometer according to claim 1, wherein the at least one sideway outlet is a slit-like exit on the electrodes of the straight linear quadrupole ion trap or between the electrodes of the straight linear quadrupole ion trap and parallel to an ion trap axis.

5. The mass spectrometer according to claim 1, further comprising an auxiliary excitation voltage source, wherein the switchable voltage source device is configured to provide the trapping high-frequency voltage for the electrodes of the straight linear quadrupole ion trap, so as to trap ions having transmitted from the quadrupole mass filter; and the auxiliary excitation voltage source is configured to provide an auxiliary resonance excitation voltage for the electrodes of the straight linear quadrupole ion trap to resonantly expel the ions in the straight linear quadrupole ion trap to the detector in an order of their mass-to-charge ratios, so as to produce a mass spectrum.

6. The mass spectrometer according to claim 3, further comprising a DC voltage source, wherein the switchable voltage source device is configured to provide the high-frequency voltage for the electrodes of the straight linear quadrupole ion trap; and the DC voltage source is configured to provide an axial potential difference between the quadrupole mass filter and the straight linear quadrupole ion trap, the potential difference accelerating ions transmitted from the quadrupole mass filter and colliding with the collision gas in the straight linear quadrupole ion trap; wherein amplitude and frequency of the high-frequency voltage enable product ions generated by collision dissociation to be captured by the straight linear quadrupole ion trap.

7. The mass spectrometer according to claim 3, further comprising a voltage source device and a controller, wherein the switchable voltage source device is configured to provide the high-frequency voltage for the electrodes of the straight linear quadrupole ion trap; the voltage source device is configured to superimpose an auxiliary excitation voltage over the electrodes of the straight linear quadrupole ion trap; and the controller is configured to control amplitude or frequency of the voltage source, so that ions transmitted from the quadrupole mass filter are affected by the auxiliary excitation voltage during capture of the straight linear quadrupole ion trap to accelerate oscillation and collide with the collision gas in the straight linear quadrupole ion trap, and product ions generated by collision dissociation are captured by the straight linear quadrupole ion trap.

8. The mass spectrometer according to claim 6, further comprising a scanning control device, configured to generate resonance excitation after fragment product ions generated by collision are captured by the straight linear quadrupole ion trap, so that the product ions are expelled to the detector in an order of mass-to-charge ratios, so as to form a second-stage mass spectrum.

9. The mass spectrometer according to claim 1, wherein the straight linear quadrupole ion trap is a digital ion trap driven by a switching voltage.

10. A mass spectrum analysis method using the mass spectrometer according to claim 1, comprising:
setting high frequency and DC voltages on the quadrupole mass filter, so as to establish a quadrupole electric field for transmitting ions in a certain mass-to-charge ratio range; and
applying a deflection voltage to the electrodes on the straight linear quadrupole ion trap, so that ions having passed through the quadrupole mass filter and entering the straight linear quadrupole ion trap, are deflected towards said at least one sideway outlet by the deflection field formed by the deflection voltage, thereby being expelled from the at least one sideway outlet radially.

11. The mass spectrum analysis method of claim 10, further comprising:
configuring the switchable voltage source to remove the deflection voltage;
applying a high-frequency voltage to the quadrupole mass filter to establish a high frequency quadrupole electric field;
applying a high frequency trapping voltage to the electrodes of the straight linear quadrupole ion trap, so as to trap ions transmitted from the quadrupole mass filter; and
selectively expelling ions in the ion trap to the detector from the outlet radially in an order of mass-to-charge ratios through auxiliary resonance excitation, so as to form a mass spectrum.

12. The tandem mass spectrum analysis method of claim 10, further comprising:
configuring the switchable voltage source to remove the deflection voltage;
applying a high-frequency voltage to the quadrupole mass filter to establish a high frequency quadrupole electric field;
applying a high frequency trapping voltage to the electrodes of the straight linear quadrupole ion trap, and setting the high frequency trapping voltage in amplitude or frequency corresponding to a trapping mass-to-charge range;
introducing collision gas to the straight linear quadrupole ion trap, and setting an axial potential difference between the quadrupole mass filter and the straight linear quadrupole ion trap, so as to accelerate ions transmitted from the quadrupole mass filter and enabling energetic collision with the collision gas in the straight linear quadrupole ion trap; and
setting DC potentials of front and rear end caps of the straight linear quadrupole ion trap, so that product ions generated by collision dissociation in the mass-to-charge ratio range are captured by the straight linear quadrupole ion trap.

13. The tandem mass spectrum analysis method of claim 10, further comprising:
configuring the switchable voltage source to remove the deflection voltage;
applying a high-frequency voltage to the quadrupole mass filter to establish a high frequency quadrupole electric field;
applying a high frequency trapping voltage to electrodes of the straight linear quadrupole ion trap, and setting DC potentials of front and rear end caps of the straight linear quadrupole ion trap, so that ions passing through the quadrupole mass filter are trapped by the straight linear quadrupole ion trap;
removing unwanted ions from the trapped ions according to their mass-to-charge ratio by applying mass selective resonance excitation or locating ions to instable regions on the a-q stability diagrams, and retaining ions in a certain mass-to-charge ratio range; and
introducing collision gas to the straight linear quadrupole ion trap, and enabling the retained ions to collide with the collision gas through resonance excitation, so as to generate fragment ions.

14. The tandem mass spectrum analysis method according to claim 12, further comprising: removing unwanted fragment ions according to their mass-to-charge ratio by applying mass selective resonance excitation or locating ions to instable region on the a-q stability diagrams, retaining ions in a certain mass-to-charge ratio range for further collision dissociation, and expelling the fragmented ions resulted in said further collision dissociation to the detector in an order of mass-to-charge ratios through resonance excitation, so as to form a third-stage mass spectrum.

15. The mass spectrum analysis method according to claim 10, further comprising:
scanning the high frequency and DC voltages of the quadrupole mass filter, and measuring current of the expelled ions to obtain a first mass spectrum.

16. The mass spectrum analysis method according to claim 15, further comprising:
configuring the switchable voltage source to remove the deflection voltage;
calculating an ion trap injection time according to a ratio of total ion signal intensity to standard signal intensity in at least a part of the mass-to-charge ratio range of the said first mass spectrum;
applying a high-frequency voltage to the quadrupole mass filter to establish a high frequency quadrupole electric field, so that ions in the mass-to-charge ratio range pass through the high frequency quadrupole electric field;
applying a high frequency trapping voltage to the electrodes of the straight linear quadrupole ion trap, and accept and trap ions transmitted from the quadrupole mass filter for the calculated ion trap injection time; and
selectively expelling ions in the straight linear quadrupole ion trap to the detector from the at least one sideway outlet radially in an order of mass-to-charge ratios through auxiliary resonance excitation, so as to produce a second mass spectrum.

17. A tandem mass spectrum analysis method using the mass spectrometer according to claim 1, comprising:
applying a high-frequency voltage to the quadrupole mass filter to establish a high frequency quadrupole electric field, providing a mass resolving quadrupole DC electric field, so that ions in a selected mass-to-charge ratio window pass through the quadrupole mass filter and the ion trap, and measuring current of the passing ions to obtain a predicted ion signal intensity in the selected mass-to-charge ratio window;
configuring the switchable voltage source to remove the deflection voltage and setting amplitude or frequency corresponding to a selected mass-to-charge ratio range for product ions on electrodes of the straight linear quadrupole ion trap;
setting an axial potential difference between the quadrupole mass filter and the straight linear quadrupole ion trap, so as to accelerate ions transmitted from the quadrupole mass filter and allow them to collide with collision gas in the straight linear quadrupole ion trap, wherein a duration of injecting ions from the quadrupole mass filter is determined by calculating the ratio of the said predicted ion signal intensity to a standard value; and setting DC potentials of front and rear end caps of the ion trap, so that product ions generated by collision dissociation in the mass-to-charge range are captured by the straight linear quadrupole ion trap.

18. A tandem mass spectrum analysis method using the mass spectrometer according to claim 1, comprising:
configuring the switchable voltage source to remove the deflection voltage;
trapping ions to be analyzed in the straight linear quadrupole ion trap;
setting high frequency and DC voltages on a quadrupole mass filter in axial tandem with the straight linear quadrupole ion trap, so as to establish a quadrupole electric field allowing ions of a certain mass-to-charge ratio range to pass;
establishing a pulse extraction voltage in an axial direction of the straight linear quadrupole ion trap, and ejecting ions from the straight linear quadrupole ion trap to enter the quadrupole mass filter;
establishing a reflection axial potential at a far end of the quadrupole mass filter, so as to turn the ions back and select precursor ions in said certain mass-to-charge ratio range during ions' forward and return journey in the mass filter;
setting new amplitude or frequency of a high frequency trapping voltage on quadrupole-forming electrodes of the straight linear quadrupole ion trap;
setting new axial potential distribution between the quadrupole mass filter and the straight linear quadrupole ion trap, so that ions returning from the quadrupole mass filter to the straight linear quadrupole ion trap are accelerated and collide with collision gas in the straight linear quadrupole ion trap; and
setting DC potentials of front and rear end caps of the straight linear quadrupole ion trap, so that product ions generated by collision dissociation in the mass-to-charge range are captured by the straight linear quadrupole ion trap.

19. The mass spectrometer according to claim 1, further comprising a switching mean allowing the electrodes of the straight linear quadrupole ion trap to be switched from the trapping high frequency voltage to the deflection voltage.

20. The mass spectrometer according to claim 19, wherein the deflection voltage is a DC voltage.

21. The mass spectrometer according to claim 7, comprising a scanning control device, configured to generate resonance excitation in at least a part of time of operation time of the straight linear quadrupole ion trap except the time the deflect field is applied, so that after fragment product ions generated by collision are captured by the straight linear quadrupole ion trap, so that the product ions are expelled to the detector in an order of mass-to-charge ratios, so as to form a second-stage mass spectrum.

22. The tandem mass spectrum analysis method according to claim 13, further comprising: removing unwanted fragment ions according to their mass-to-charge ratio by applying mass selective resonance excitation or locating ions to instable region on the a-q stability diagrams, retaining ions in a certain mass-to-charge ratio range for further collision dissociation, and expelling the fragmented ions resulted in said further collision dissociation to the detector in an order of mass-to-charge ratios through resonance excitation, so as to form a third-stage mass spectrum.

23. A mass spectrometer, comprising:
an ion source in a vacuum environment;
a quadrupole mass filter located downstream of the ion source;
a straight linear quadrupole ion trap located downstream of the mass filter and having at least one sideway outlet, wherein the straight linear quadrupole ion trap is the only one ion trap of the mass spectrometer;
a detector disposed at a side of the straight linear quadrupole ion trap, configured to receive ions extracted from the sideway outlet of the straight linear quadrupole ion trap;
a pulse gas providing device, configured to provide required cooling gas and collision gas for the straight linear quadrupole ion trap; and
at least a switchable voltage source device, configured to switchably generate a trapping high frequency voltage or a deflection voltage applied to the electrodes of the straight linear quadrupole ion trap, wherein at least in part of the operation time of the straight linear quadrupole trap, the switchable voltage source device delivers voltages to generate a radial deflection field in the straight linear quadrupole ion trap, and the radial deflection field causes ions selected by the quadrupole mass filter for their mass to charge ratio and entering the straight linear quadrupole ion trap to be continuously deflected towards the sideway outlet, thereby temporally convert the straight linear quadrupole ion trap as a continuous ion bender which expel the selected ions radially out through the sideway outlet without being accumulated or without mass-selective treating in the straight linear quadrupole ion trap.

* * * * *